(12) United States Patent
Race et al.

(10) Patent No.: US 12,340,904 B2
(45) Date of Patent: Jun. 24, 2025

(54) PATIENT MONITORING AND CARE

(71) Applicant: Atlas Lift Tech, Inc., San Ramon, CA (US)

(72) Inventors: Eric Race, Miami, FL (US); Anton Vishnyak, San Ramon, CA (US); Nicholas Preston Baker, New York, NY (US); Carter Calvin West, Pioneer, CA (US); Maythem Alsodani, Brooklyn, NY (US); Joshua Scott Franco Garcia, Oakland, CA (US)

(73) Assignee: Atlas Lift Tech, Inc., San Ramon, CA (US)

( * ) Notice: Subject to any disclaimer, the term of this patent is extended or adjusted under 35 U.S.C. 154(b) by 287 days.

(21) Appl. No.: 17/692,373

(22) Filed: Mar. 11, 2022

(65) Prior Publication Data
US 2023/0005613 A1   Jan. 5, 2023

Related U.S. Application Data

(60) Provisional application No. 63/159,952, filed on Mar. 11, 2021.

(51) Int. Cl.
*G16H 40/67* (2018.01)
*G16H 10/60* (2018.01)
*G16H 40/20* (2018.01)

(52) U.S. Cl.
CPC ............ *G16H 40/67* (2018.01); *G16H 10/60* (2018.01); *G16H 40/20* (2018.01)

(58) Field of Classification Search
CPC ......... G16H 40/67; G16H 10/60; G16H 40/20
USPC ........................................... 705/2–3
See application file for complete search history.

(56) References Cited

U.S. PATENT DOCUMENTS

| | | | |
|---|---|---|---|
| 9,655,546 B2 | 5/2017 | Shen | |
| 9,728,061 B2 | 8/2017 | Shen | |
| 10,004,447 B2 | 6/2018 | Shen | |
| 10,020,075 B2 | 7/2018 | Perlman | |
| 10,140,837 B2 | 11/2018 | Shen | |
| 10,258,258 B2 | 4/2019 | Larson | |
| 10,265,010 B2 | 4/2019 | Larson | |
| 10,453,157 B2 * | 10/2019 | Kamen | A61M 5/142 |
| 10,497,474 B2 | 12/2019 | Perlman | |

(Continued)

OTHER PUBLICATIONS

Gale Healthcare Solutions, 10 Best Nursing Technologies for Improving Patient Care, https://galehealthcaresolutions.com/10-best-nursing-technologies-for-improving-patient-care/, Feb. 24, 2021 (Year: 2021).*

*Primary Examiner* — Joy Chng
(74) *Attorney, Agent, or Firm* — Ahmann Kloke LLP

(57) ABSTRACT

Disclosed is a system that includes a computer-readable medium (CRM) coupling a variety of devices. The variety of devices can include one or more patient wearable sensor devices, a paired patient device, and a patient devices docking station. The system can also include a smart patient care cart, a nurse station, a lift tracker station, and/or an agnostic aggregation station. The system can also include a patient datastore, a facility datastore, a caregiver datastore, a device datastore, a patient state datastore, a patient management datastore, a facility management datastore, a caregiver management datastore, an electronic health record (EHR) system datastore, a health/fitness datastore, and an agnostic aggregation datastore.

18 Claims, 10 Drawing Sheets

(56) References Cited

U.S. PATENT DOCUMENTS

| | | |
|---|---|---|
| 10,535,432 B2 | 1/2020 | Perlman |
| 10,588,565 B2 | 3/2020 | Larson |
| 10,631,732 B2 | 4/2020 | Larson |
| 10,682,076 B2 | 6/2020 | Larson |
| 10,729,357 B2 | 8/2020 | Larson |
| 10,758,162 B2 | 9/2020 | Shen |
| 10,874,330 B2 | 12/2020 | Larson |
| 10,888,251 B2 | 1/2021 | Larson |
| 10,892,053 B2 | 1/2021 | Perlman |
| 10,912,491 B2 | 2/2021 | Shen |
| 11,049,612 B2 | 6/2021 | Perlman |
| 11,272,860 B2 | 3/2022 | Larson |
| 11,278,237 B2 | 3/2022 | Larson |
| 11,317,830 B2 | 5/2022 | Shen |
| 11,369,309 B2 | 6/2022 | Larson |
| 11,456,074 B2 | 9/2022 | Perlman |
| 11,794,221 B2 * | 10/2023 | Maloley .................. B62B 3/005 |
| 2015/0227127 A1 * | 8/2015 | Miller ..................... G16H 20/13 |
| | | 700/244 |
| 2019/0374133 A1 * | 12/2019 | Shen .................. G08B 21/0446 |
| 2020/0135334 A1 * | 4/2020 | Rajasekhar ............. G10L 15/26 |
| 2022/0149640 A1 * | 5/2022 | Hsu ....................... H02J 7/0044 |

* cited by examiner

PATIENT MONITORING AND CARE

DETAILED DESCRIPTION

Figure 1:
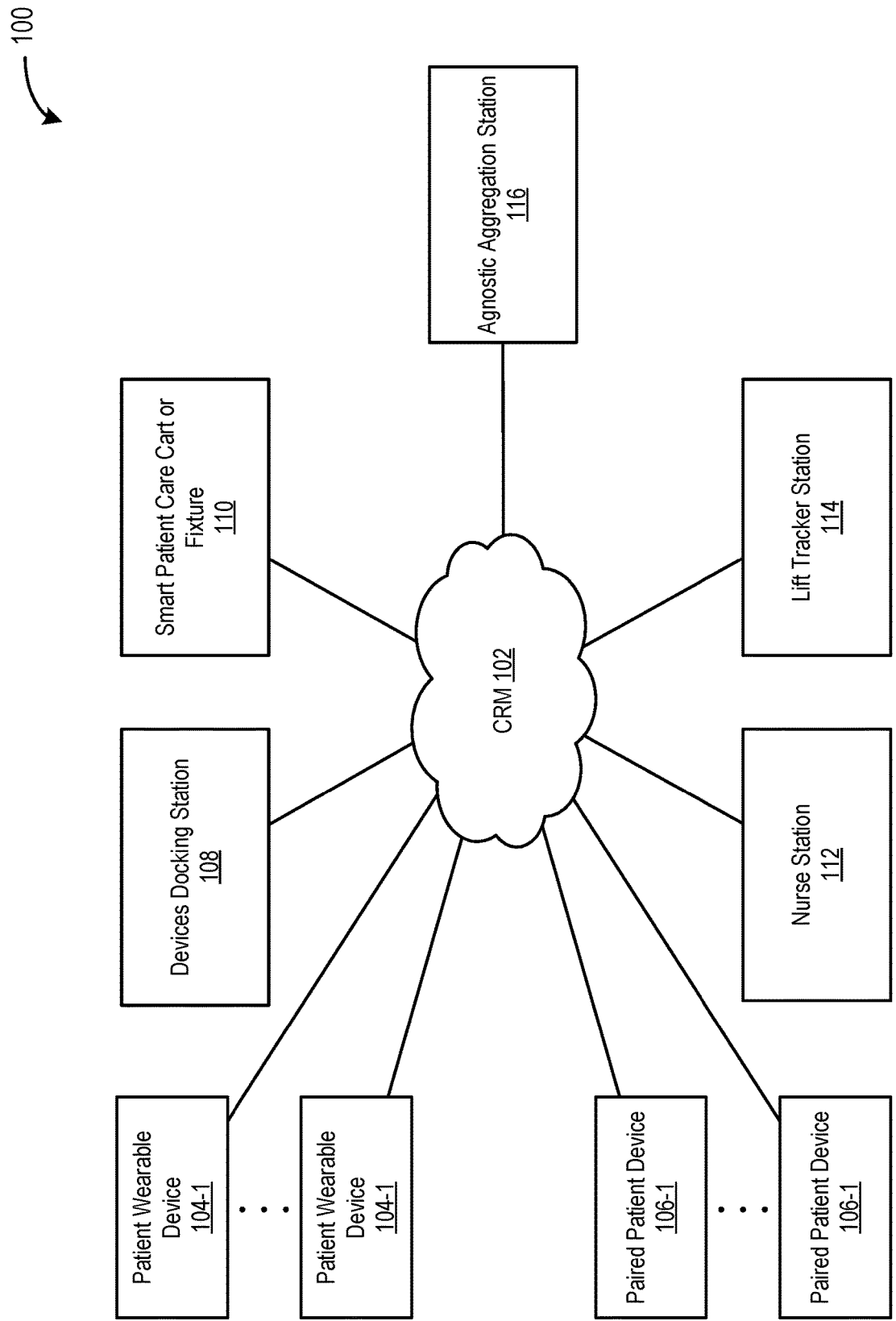
FIGS. 1 and 2 are diagrams of an example of a patient monitoring and care system.
Figure 2:
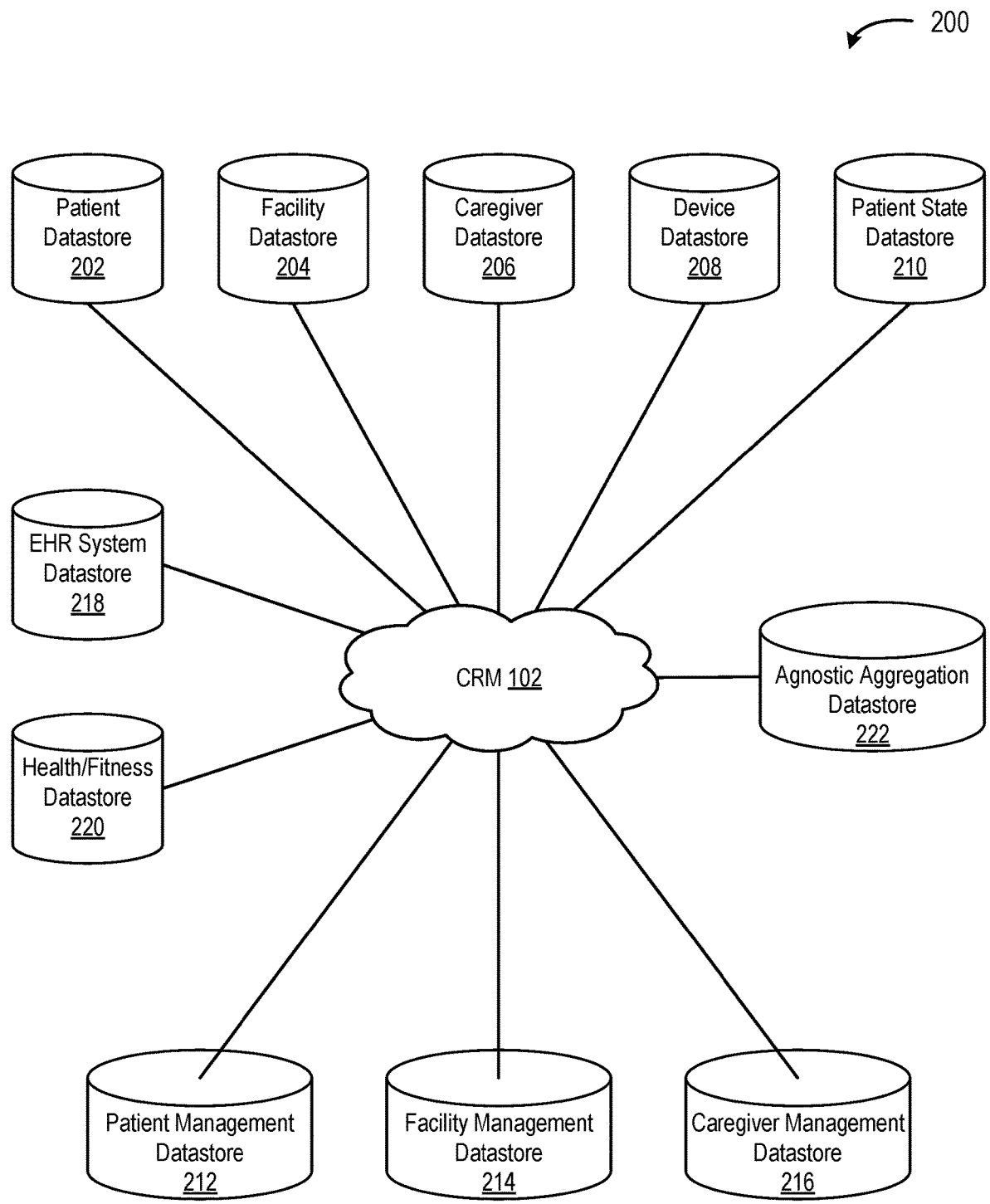

FIGS. 1 and 2 diagrams 100 and 200 of an example of a patient monitoring and care system. The diagram 100 includes a computer-readable medium (CRM) 102, a patient wearable sensor device 104-1 to 104-*n* (collectively, the wearable devices 104) coupled to the CRM 102, a paired patient device 106 coupled to the CRM 102, a patient devices docking station 108 coupled to the CRM 102, a smart patient care cart 110 coupled to the CRM 102, a nurse station 112 coupled to the CRM 102, a lift tracker station 114 coupled to the CRM 102, and an agnostic aggregation station 116 coupled to the CRM 102. The diagram 200 includes the CRM 102, a patient datastore 202 coupled to the CRM 102, a facility datastore 204 coupled to the CRM 102, a caregiver datastore 206 coupled to the CRM 102, a device datastore 208 coupled to the CRM 102, a patient state datastore 210 coupled to the CRM 102, a patient management datastore 212 coupled to the CRM 102, a facility management datastore 214 coupled to the CRM 102, a caregiver management datastore 216, an electronic health record (EHR) system datastore 218 coupled to the CRM 102, a health/fitness datastore 220 coupled to the CRM 102, and an agnostic aggregation datastore 222 coupled to the CRM 102.

The CRM 102 is intended to represent a computer system or network of computer systems. A "computer system," as used herein, may include or be implemented as a specific purpose computer system for carrying out the functionalities described in this paper. In general, a computer system will include a processor, memory, non-volatile storage, and an interface. A typical computer system will usually include at least a processor, memory, and a device (e.g., a bus) coupling the memory to the processor. The processor can be, for example, a general-purpose central processing unit (CPU), such as a microprocessor, or a special-purpose processor, such as a microcontroller.

Memory of a computer system includes, by way of example but not limitation, random access memory (RAM), such as dynamic RAM (DRAM) and static RAM (SRAM). The memory can be local, remote, or distributed. Non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. During execution of software, some of this data is often written, by a direct memory access process, into memory by way of a bus coupled to non-volatile storage. Non-volatile storage can be local, remote, or distributed, but is optional because systems can be created with all applicable data available in memory.

Software in a computer system is typically stored in non-volatile storage. Indeed, for large programs, it may not even be possible to store the entire program in memory. For software to run, if necessary, it is moved to a computer-readable location appropriate for processing, and for illustrative purposes in this paper, that location is referred to as memory. Even when software is moved to memory for execution, a processor will typically make use of hardware registers to store values associated with the software, and a local cache that, ideally, serves to speed up execution. As used herein, a software program is assumed to be stored at an applicable known or convenient location (from non-volatile storage to hardware registers) when the software program is referred to as "implemented in a computer-readable storage medium." A processor is considered "configured to execute a program" when at least one value associated with the program is stored in a register readable by the processor.

In one example of operation, a computer system can be controlled by operating system software, which is a software program that includes a file management system, such as a disk operating system. One example of operating system software with associated file management system software is the family of operating systems known as Windows from Microsoft Corporation of Redmond, Wash., and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

The bus of a computer system can couple a processor to an interface. Interfaces facilitate the coupling of devices and computer systems. Interfaces can be for input and/or output (I/O) devices, modems, or networks. I/O devices can include, by way of example but not limitation, a keyboard, a mouse or other pointing device, disk drives, printers, a scanner, and other I/O devices, including a display device. Display devices can include, by way of example but not limitation, a cathode ray tube (CRT), liquid crystal display (LCD), or some other applicable known or convenient display device. Modems can include, by way of example but not limitation, an analog modem, an IDSN modem, a cable modem, and other modems. Network interfaces can include, by way of example but not limitation, a token ring interface, a satellite transmission interface (e.g. "direct PC"), or other network interface for coupling a first computer system to a second computer system. An interface can be considered part of a device or computer system.

Computer systems can be compatible with or implemented as part of or through a cloud-based computing system. As used in this paper, a cloud-based computing system is a system that provides virtualized computing resources, software and/or information to client devices. The computing resources, software and/or information can be virtualized by maintaining centralized services and resources that the edge devices can access over a communication interface, such as a network. "Cloud" may be a marketing term and for the purposes of this paper can include any of the networks described herein. The cloud-based computing system can involve a subscription for services or use a utility pricing model. Users can access the protocols of the cloud-based computing system through a web browser or other container application located on their client device.

A computer system can be implemented as an engine, as part of an engine, or through multiple engines. As used in this paper, an engine includes at least two components: 1) a dedicated or shared processor or a portion thereof; 2) hardware, firmware, and/or software modules executed by the processor. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors, or a first engine and a second engine can share one or more processors with one another or other engines. Depending upon implementation-specific or other considerations, an engine can be centralized, or its functionality distributed. An engine can include hardware, firmware, or software embodied in a computer-readable medium for execution by the processor. The processor transforms data into new data using implemented data structures and methods, such as is described with reference to the figures in this paper.

The engines described in this paper, or the engines through which the systems and devices described in this paper can be implemented, can be cloud-based engines. As used in this paper, a cloud-based engine is an engine that can run applications and/or functionalities using a cloud-based computing system. All or portions of the applications and/or functionalities can be distributed across multiple computing devices and need not be restricted to only one computing device. In some embodiments, the cloud-based engines can execute functionalities and/or modules that end users access through a web browser or container application without having the functionalities and/or modules installed locally on the end-users' computing devices.

As used in this paper, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a general- or specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. As used in this paper, a data structure is associated with a way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described in this paper, can be cloud-based datastores. A cloud based datastore is a datastore that is compatible with cloud-based computing systems and engines.

Assuming a CRM includes a network, the network can be an applicable communications network, such as the Internet or an infrastructure network. The term "Internet" as used in this paper refers to a network of networks that use certain protocols, such as the TCP/IP protocol, and possibly other protocols, such as the hypertext transfer protocol (HTTP) for hypertext markup language (HTML) documents that make up the World Wide Web ("the web"). More generally, a network can include, for example, a wide area network (WAN), metropolitan area network (MAN), campus area network (CAN), or local area network (LAN), but the network could at least theoretically be of an applicable size or characterized in some other fashion (e.g., personal area network (PAN) or home area network (HAN), to name a couple of alternatives). Networks can include enterprise private networks and virtual private networks (collectively, private networks). As the name suggests, private networks are under the control of a single entity. Private networks can include a head office and optional regional offices (collectively, offices). Many offices enable remote users to connect to the private network offices via some other network, such as the Internet.

The patient wearable devices 104 are intended to represent devices that include sensors or trackable components used to facilitate a determination regarding patient environmental, physiological (including body position, temperature, pulse, or the like), and/or other data associated with the patent to which the devices are affixed. The patient wearable devices may or may not include multiple functionally similar devices, one of which can be worn while the other(s) are (re)charged. In a specific implementation, the patient wearable devices 104 include a sensor suite, such as a three-axis accelerometer and an orientation sensor, and a datastore of detected stimuli. It could also include a gyroscope and a magnetometer, which can improve the sensor up to a six-axis sensor (with either a gyroscope or magnetometer) or nine-axis sensor (with both). Without a magnetometer and/or gyroscope, it may be desirable to use a technique called dead reckoning to determine patient orientation, and a dead reckoning engine could be implemented on the paired patient devices 106 in such an embodiment. The patient wearable devices 104 can also include a radio frequency (RF) transceiver. In an implementation that includes an RF transceiver, the datastore of detected stimuli can be relatively small (and may or may not comprise only volatile storage), particularly if the datastore contents are transmitted with sufficient speed to free up space within the datastore; the datastore can also overwrite old data to free up space on the device. In some implementations, such as where the patient wearable devices 104 include something similar to a smart watch, the datastore can be relatively large, which can enable the patient wearable devices 104 to send data from the datastore in batches, preprocess the data to reduce transmission size, determine whether data parameters exceed an alert threshold prior to sending the data via an RF transmitter (which can include e.g., deleting redundant, erroneous, or otherwise ultralow priority data and/or maintaining historic data deemed time-insensitive or low priority for uploading later when the device is operationally connected to a docking station), or take other actions that reduce resource consumption (e.g., of battery, wireless bandwidth, or other resources). In an implementation that includes an RF transceiver, a subset (which can include all) of the patient wearable devices 104 can include a configurable pairing module that is used to pair one or more of the patient wearable devices 104 to some other device, such as a caregiver mobile device, docking station communications device, or some other paired endpoint device.

It may be noted that the patient wearable devices 104 can include an RF transmitter or RF transponder, though the term "RF transceiver" is intended to include devices that act as RF transponders unless explicitly indicated to be an RF transponder and, of course, an RF transceiver includes an RF transmitter (in addition to an RF receiver). In an implementation that includes an RF transponder, one or more of the patient wearable devices 104 can include an RFID tag that includes an RF transponder that is triggered by an electromagnetic interrogation pulse from an RFID reader device. RFID tags can be used for the purpose of inventory; a pairing module is more likely to be utilized by patient wearable devices 104 when uniquely associated with a patient, though this is not an explicit requirement.

Instead or in addition, sensors capable of determining patient position using electromagnetic waves (e.g., visible, infrared, or ultraviolet light), acoustic waves, or other stimuli, are deployed near a patient to improve physiological state precision and/or accuracy. Such technologies can assist in interpreting sensor data regarding patient position, analyze facial features to determine emotional state, detect motion, listen for sounds (e.g., breathing, verbalizations, or the like), or perform remote temperature measurements, to name a few examples.

In a specific implementation, the patient wearable devices 104 are purposefully built or configured Internet of Things (IoT) devices, or collections of IoT devices. In being purposely built IoT devices, the patient wearable devices 104 are built to have specific operational parameters. For example, a patient wearable devices 104 may be configured to provide data from a three dimensional accelerometer and orientation sensor. In being purposely configured IoT devices, the patient wearable devices 104 can be configured to operate according to specific operational parameters in accordance with input from a human or artificial agent. For example, patient wearable devices 104 can include a protocol to curate detected stimuli in accordance with a data reduction algorithm. As another example, an agent can specify an IoT device should retain raw data until docked.

The paired patient devices 106 are intended to represent devices capable of receiving measured or estimated patient environmental, physiological (including body position, temperature, pulse, or the like), and/or other data either directly from the patient wearable devices 104 or indirectly through a network coupled to both the patient wearable devices 104 and the paired patient devices 106. The environmental, physiological, or other data can be referred to as data included in patient state data, which represents measurement data of a patient or the environment around the patient, all of which can be characterized as data associated with a patient. Unless context dictates otherwise, historical patient state is considered part of current patient state at least in part because state transitions of complex systems, such as the human body, can be diagnostically relevant when assessing current patient state. (In addition to data representative of historical patient state, patient state data can include predicted, target, or other non-historical patient state, but unless context dictates otherwise patient state is intended to represent current patient state.) The paired patient devices 106 are referred to as "paired" because, in the example of FIG. 1, the paired patient devices 106 are paired with at least one of the patient wearable devices 104. Advantageously, pairing enables the utilization of user-friendly, ubiquitous, secure communications technology that should require little or no training for relevant parties. It may be noted that communications technologies other than pairing can be used to transmit data from the patient wearable devices 104, either directly or indirectly, to end user devices. For example, instead or in addition, the paired patient devices 106 can be configured as stations in a mesh network, and, as such, referred to as "mesh networked patient devices."

In a specific implementation in which mesh network patient devices are utilized, the patient wearable device 104 can bounce to any of the paired patient device 106 and the paired patient devices 106 can communicate directly with or forward messages from one another to the nurse station 112 (or some other applicable station to which all of the paired patient devices 106 ultimately report). In a specific implementation, the paired patient devices 106 are configured upon startup, e.g., by having them scan a QR code to request a unique certificate that allows the device to be trusted within a facility or portion thereof. Advantageously, PKI can be used to enable the paired patient devices 106 to trust one another without maintaining a list. It may be desirable, however, to maintain a revocation list, which can be updated from time to time (e.g., daily).

The paired patient devices 106 can be referred to as "endpoint" because, in the example of FIG. 1, the paired patient devices 106 are used as end-user devices by caregivers who monitor a patient. Such devices can include smartphones, tablets, notebook computers, laptop computers, desktop computers, IoT devices, and/or other devices that are configured to send and receive information via the CRM 102. More generally, however, the paired patient devices 106 can be implemented as network connected devices with a screen (to enable monitoring) and a battery (to enable the device to operate when unplugged, which is important in certain care facility implementations). Such devices can be specially-purposed with the installation of an application, though a general purpose browser may be adequate, depending upon the implementation, for sending relevant data to and receiving relevant data from other components illustrated in the diagram 100.

In a specific implementation, the paired patient devices 106 include a bedside tablet computer that is paired with one or more of the patient wearable devices 104. More generally, the paired patient devices 106 can include a tablet computer that is within short-range RF communication with the patient wearable devices 104, which can include being in the same room as a patient (with or without a bed), just outside a patient's room, or within the same building as a patient (e.g., for a patient for which care is being provided in his or her home). Instead or in addition, the paired patient devices 106 can include a caregiver smartphone that is paired with the patient wearable devices 104.

It may be noted that in most of the description provided in this paper, reference is made to a single paired patient device. However, there are implementations in which more than one such device is used. For example, a room may have a single patient device docking station but two beds. In such a scenario, rather than having multiple patient-dedicated docking stations, you could have a single docking station with two paired endpoint devices, one per bed. Continuing this scenario, you could have multiple agnostic patient wearable devices that you pair with the applicable end point device when deploying for a specific patient.

The devices docking station 108 is intended to represent one or more devices that provides a simplified way of "plugging-in" or docking a mobile device. In this context, docking means putting the devices docking station 108 into an applicable configuration vis-à-vis the patient wearable devices 104, such as by connecting, nesting, housing, holding, or otherwise coupling at least one of the patient wearable devices 104 to the devices docking station 108. Because a wide range of dockable devices—from mobile telephones to wireless mice—have different connectors, power signaling, and uses, the devices docking station 108 may be specifically designed for the patient wearable devices 104.

In a specific implementation, the devices docking station 108 is configured to recharge the patient wearable devices 104 when docked. In an implementation in which there are multiple patient wearable devices 104, the devices docking station 108 can dock all the patient wearable devices 104 devices when in an undeployed mode and all the patient wearable devices 104 except those being worn by a patient when in a deployed mode. In an implementation in which an on-device datastore includes detected stimuli (or processed data) from when a first of the patient wearable devices 104 is deployed (e.g., worn by a patient), data from the datastore may or may not also be downloaded from the first patient wearable device when it is operationally connected to the devices docking station 108.

In a specific implementation, the devices docking station 108 is configured to recharge the paired patient devices 106 when docked. In an alternative, the devices docking station 108 is configured to recharge both the patient wearable devices 104 and the paired patient devices 106 when docked. To the extent the patient wearable devices 104 and the paired patient devices 106 are different, the devices docking station 108 may be specifically designed to dock the devices using different docking technologies.

Mobile devices can dock and undock hot, cold or standby, depending on the capabilities of the system. In a cold dock or undock, a mobile device is shut down before docking/undocking. In a hot dock or undock, a mobile device remains running when docked/undocked. Standby docking or undocking, an intermediate style used in some designs, allows a mobile device to be docked/undocked while powered on, but requires that it be placed into a sleep mode prior to docking/undocking. In a specific implementation, the devices docking station 108 allows a docked one of the patient wearable devices 104 to become a substitute for a desktop computer. In an alternative, the devices docking station 108 allows a docked one of the paired patient devices 106 to become a substitute for a desktop computer. In another alternative, the devices docking station 108 allows a docked one of the patient wearable devices 104 or a docked one of the paired patient devices 106 to become a substitute for a desktop computer.

In a specific implementation, each of the paired patient devices 106 are incorporated into respective devices docking stations. In such an implementation, the devices docking stations with the incorporated paired patient devices 106 can be referred to as "bedside" patient mobility monitors. Of course, the patient mobility monitor need not explicitly be at the bedside of a patient (e.g., it could be at a nurse station operationally connected to the patient wearable devices 104 via a wireless network, such as a mesh network).

The smart patient care cart or fixture 110 is intended to represent a mobile unit or fixture that includes devices useful to patient care providers. For example, the smart patient care cart or fixture 110 includes UV disinfection technology; devices can be placed within a chamber that receives UV radiation powered by a battery connected to the smart patient care cart or fixture 110 or via an electrical outlet when the smart patient care cart or fixture 110 is stationary. If the smart patient care cart or fixture 110 is a fixture, the necessity of a battery is diminished, but in some care facility implementations, it is desirable to ensure the device is mobile, increasing the importance of the battery. Other applicable disinfection methodologies beyond UV can be employed, such as ethylene oxide (EO) sterilization or electron beam sterilization. As another example, the smart patient care cart or fixture 110 includes a computer coupled to a network for sending and receiving data regarding inventory on the smart patient care cart or fixture 110, such as items that should be stocked on the smart patient care cart or fixture 110 (and an indication whether they are), items that have been deployed from the smart patient care cart or fixture 110, results of proximity detection of devices tagged with RFID, indications regarding which devices to deploy depending upon patient state, or the like.

In a specific implementation, the smart patient care cart 110 can include slings with RFID tags attached as a patch or embedded during manufacturing, which can be lost and are relatively expensive. By tagging the slings and maintaining a log of deployment at the smart patient care cart 110, the deployment, proximity detection, and recovery of slings is improved such that the slings are lost less frequently. Also, there are also hundreds of different types of slings, not all of which are appropriate for a specific patient, intended patient readjustment (or lift), or other applicable situation. If appropriately configured, the smart patient care cart 110 can even provide instructions to a patient care provider regarding which sling to deploy for a patient depending upon patient state.

The nurse station 112 is intended to represent a unit at which devices on a floor, wing, building, or other designated space can be monitored. In a hospital or other health care facility, a workstation is often used by a nurse for something other than patient positioning. As used in this paper, the nurse station 112 is intended to represent only the engines and datastores that utilize the technologies described herein. For example, in a specific implementation, the nurse station 112 includes an output device (e.g., a dashboard and potentially a speaker) for providing patient position information and an input device (e.g., a button) for summoning lift technicians that is distinct and separate from devices used by a nurse in a conventional nursing station. Where a distinction is desired, the conventional nurse workstation can be referred to as a "master nurse workstation" and the nurse station 112 as a "nurse station."

In a specific implementation, the output device of the nurse station 112 displays a graphic of patient position in real time and provide alerts depending upon patient state. Factors considered in displaying the graphic and providing alerts include patient body shape, positions to avoid (including, e.g., a clear warning about disallowed positions), risk assessment modelling (e.g., Scott Triggers or non-proprietary assessment tools), indications where to place one or more of the patient wearable devices 104, battery level alerts for the patient wearable devices 104, countdown to next repositioning, a next (target) position, a summary of how long in each position (typically including medical terms for each position), timeline of positions, and how wiggly a patient is over time. The output device of the nurse station 112 may or may not also display information sufficient to identify and track a lift technician, including transit time or time with patient, and to obtain lift technician notes (including special notes if applicable) and data from the patient wearable devices 104, paired patient devices 106, the patient devices docking station 108, and/or the smart patient care cart 110, though some or all of such information may instead be made available through the lift tracker station 114 and not the nurse station 112, depending upon implementation-, configuration-, and/or preference-specific factors.

In a specific implementation, the input device of the nurse station 112 includes a touch screen (or other applicable technology, such as a keyboard and/or mouse) through which equipment can be requested from vendors and lift technicians summoned; lift technicians can respond with recommended equipment suggestions and be automatically notified when the equipment arrives. Lift technicians can also be auto-directed, depending upon implementation-, configuration-, and/or preference-specific factors, making it unnecessary for a patient care provider or human agent thereof to explicitly make a request in at least some circumstances after the rules for auto-direct are instantiation (which can include initial instantiation).

In a specific implementation, the nurse station 112 enables a human or artificial agent to monitor multiple patients. The number of patients monitored at the nurse station 112 depends upon implementation-, configuration-, and preference-specific factors, but can represent a wing, a floor, multiple wings or floors, an entire facility, or some subset of areas within a facility with patients. As such, the nurse station can be characterized as a "wing," "floor," "facility," or more generally a "unit" patient mobility monitor.

The lift tracker station 114 is intended to represent a unit at which lift technology information, devices, and people are monitored. The lift tracker station 114 can have access to some or all of the information available to the nurse station 112. In addition, lift technicians can enter notes (including special notes if applicable) via a mobile device.

The agnostic aggregation station 116 is intended to represent a unit at which aggregated data about patients, with personally identifying information (PII) and any other information that is deemed to be toxic when freely shared across institutions, has been removed. Such data is referred to herein as "toxic" data. Toxic data may or may not include facility and/or caregiver data and, to the extent there are multiple different agnostic aggregation stations, some data may be considered toxic for one (e.g., patient, facility, or caregiver information about a facility not under an agent's purview) but not for another (e.g., patient, facility, or caregiver information about a facility or facilities under an agent's purview). The agnostic aggregation station 116 can have access to some or all of the information available to the nurse station 112, minus the toxic data. This data can be used to monitor the success of facilities in providing patient mobility, cost-effective use of resources, and for other purposes that are benefited by the sharing of patient mobility and other (agnostic) patient-related data, facility data, and caregiver data.

In an example of operation, a first patient wearable device of the patient wearable devices 104 is paired with a first paired patient device of the paired patient devices 106 using configurable pairing technology. The first patient wearable device is then affixed to a patient in a location suitable for providing accurate estimates of patient position, such as on the upper chest (or the back for uncooperative patients). In an alternative, multiple patient wearable devices of the patient wearable devices 104, including the first patient wearable device, are affixed to a patient in different locations. The technology for affixing these devices to a patient is described in more detail below.

In this example of operation, the first patient wearable device collects raw patient position data via a three axis accelerometer and an orientation sensor. Depending upon implementation-, configuration-, and/or preference-specific factors, the raw patient position data can be curated to reduce the amount of data that is transmitted. For example, if no change of position is detected, the first patient wearable device may not send the data. Due to the quality of storage devices available, the historical raw data may be maintained until the first patient wearable device is docked, at which point the data can be transmitted to ensure all historical data is made available. If storage capacity is limited, the first patient wearable device can either transmit all raw patient position data or delete some of it.

In this example of operation, the first patient wearable device wirelessly transmits patient position data (which may include all or a subset of the raw patient position data) to the first paired patient device using an RF transceiver and secure communications to the first paired patient device. In a typical implementation, the first paired patient device would be located at a bedside table of the patient, on an IV pole, within the same room, at the entrance to the room, or at some other location that enables the use of low-power transmission. As such, the first patient wearable device can be characterized as a short-range device (SRD). An SRD, described by ECC Recommendation 70-03, which is incorporated by reference, is a radio-frequency transmitter device used in telecommunication for the transmission of information, which has low capability of causing harmful interference to other radio equipment. Short-range devices are low-power transmitters typically limited to 25-100 mW effective radiated power (ERP) or less, depending on the frequency band, which limits their useful range to few hundred meters, and do not require a license from their users. Short-range wireless technologies include Bluetooth, Wi-Fi, near-field communication (NFC), ultra-wideband (UWB) and IEEE 802.15.4, which is incorporated by reference. Because the first paired patient device is located near the first patient wearable device in this example, the transmission can be via a low-power transmission protocol, which increases battery life of and decreases the heat generated by the first patient wearable device.

In this example of operation, the first paired patient device provides the patient position data to the patient datastore 202. The patient datastore 202 can initially include patient data that would normally be maintained at a patient care facility, though access to some data may be restricted. For the purposes of this paper, the patient datastore 202 is intended to represent all available patient data, with the understanding it is possible some useful information could conceivably be made unavailable due to privacy or other concerns. As such, the patient datastore 202 can be referred to as including "available patient data" while a patient datastore with unavailable data can be referred to as including "unavailable patient data," even if the two different datastores could be stored, e.g., in the same database. The patient datastore 202 may include data that is available to a nurse, to a lift technician, or to another party, to the exclusion of at least one other party; to the extent such data is available to at least one party acting pursuant to techniques described in this paper, the data is considered available data and, as such, included in the patient datastore 202.

In this example of operation, the first paired patient device and a second patient wearable device of the patient wearable devices 104 are docked at the patient devices docking station 108. The first paired patient device can be operable as a computer while docked or removed for use when a patient care provider or human agent thereof wishes to pick it up. The second patient wearable device is docked for the primary purpose of ensuring it is charged when it comes time to replace the first patient wearable device with the second patient wearable device (at which time the first patient wearable device would be docked for charging). Alternatively, a second patient wearable device could be included in the smart patient care cart 110 and replaced when a patient care provider or human agent thereof visits the patient.

In this example of operation, a patient care provider or human or artificial agent thereof (referred to collectively as a nurse) has access to the patient datastore 202 through the nurse station 112. The nurse also has access to the facility datastore 204, which includes information about the facility, such as a floorplan that includes rooms and other applicable locations, beds and other furniture or fixtures; the facility datastore 204 enables the nurse to locate furniture, patients, patient care providers and other personnel, and devices within the facility using the nurse station 112. The nurse also has access to the caregiver datastore 206, which includes information about patient care providers, such as identification, role, or the like, as well as associations between patient care providers and patients and patient care providers and the facility. In alternatives, some or all of the datastores 202-206 can instead or in addition be accessed by a lift technician or human or artificial agent thereof.

In this example of operation, a lift technician or human or artificial agent thereof (referred to collectively as a lift technician team, with the understanding there could conceivably be a single lift technician on site) has access to the device datastore 208, which includes information about the patient wearable devices 104, the paired patient devices 106, and the patient device docking station 108. To the extent the lift technician team also has access to some or all of the datastores 202-206 the lift technician team can determine associations between the devices and a patient, the devices within the facility, and/or the devices and a patient care provider.

In this example of operation, the patient state datastore 210 is intended to be available to both the nurse and the lift technician team. (To the extent patient data is unavailable to the nurse or the lift technician team, the unavailable data can be considered part of the patient datastore 202, which may be accessible to only one of the interested parties.) The engine responsible for updating the patient state datastore 210 can be included in the nurse station 112, the lift tracker station 114, or distributed (or redundant) across both. The patient state datastore 210 includes a timeline of positions as derived from patient position data detected by at least the first patient wearable device and provided through the first paired patient device, as well as a future timeline of target positions. Importantly, other information is made available in association with patient state, including high risk factors for specific patients in real time, such as low mobility but apparently getting out of bed, exhibiting pre-fall warning signs. Other information associated with patient risk and positioning issues include attitude (e.g., stubbornness), sex or gender (e.g., male), age (e.g. over 60 years of age), medication effects, including side effects (e.g., dizziness), length of stay, DVT, previous falls, environmental conditions (e.g., IV pole that could trip a patient), or the like. Most health care institutions that use pressure ulcer risk assessment tools use either the Braden Scale or Norton Scale, with the Braden Scale being most widely used. The copyrighted tool is available at http://www.bradenscael.com.braden.pdf, which is incorporated by reference.

In this example of operation, the patient management datastore 212 is updated at the nurse station 112 and the lift tracker station 114 to indicate actions taken in association with a patient or scheduled for a patient, which can include lifting, medication, food and liquid intake, surgery or other treatment, observations, or the like.

In this example of operation, the facility management datastore 214 is updated at the nurse station 112 and the lift tracker station 114 to indicate room scheduling, utilization of facility resources, and requests for and receipt of additional facility resources. Some facility management can be automated by using location technology to identify physical resources within the facility.

In this example of operation, the caregiver management datastore 216 is updated at the nurse station 112 and the lift tracker station 114 to indicate work shifts, requests for lift technician assistance, speed of response, time with patient, notes regarding actions taken by lift technicians, and the like. Some caregiver management can be automated by using location technology to identify caregivers within a facility (and in proximity to a patient).

At any point in the example of operation provided above, relevant parties can access the EHR system datastore 218, assuming appropriate permissions.

In this example of operation, a patient may be discharged but retain access to the health/fitness datastore 220. The health/fitness datastore 220 can be updated with wearable devices, such as Fitbit® devices. As such, the health/fitness datastore 220 can include, e.g., a Fitbit Health Account. To the extent contents of the health/fitness datastore 220 remain available to a nurse station 112, a lift tracker station 114, or an agnostic aggregation station 116, the data collected from wearables can continue to be monitored for the same mission-specific purposes (e.g., dispatching lift technicians to a person who is at home, analyzing success rates for certain treatments using agnostic data, etc.).

In this example of operation, data collected in any datastore that can be made non-toxic can be saved in the agnostic aggregation datastore 222. Agents of the agnostic aggregation station 116 can access the agnostic aggregation datastore 222 to monitor aggregated patient success rates, research improved healthcare techniques, assist in implementing cost-effective measures in facilities, or the like.

Figure 3:
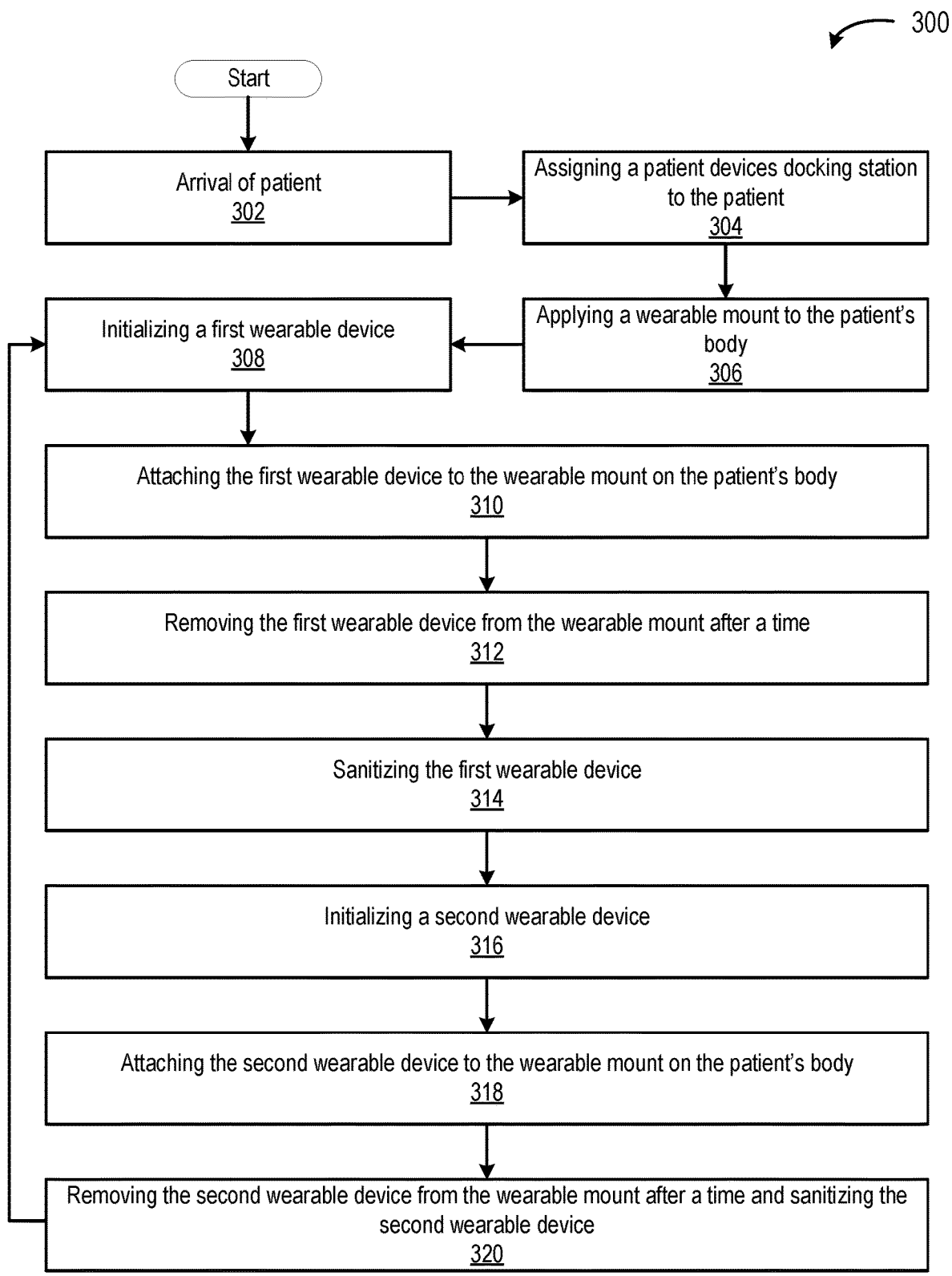
FIG. 3 is a flowchart of an example of a patient monitoring and care method.

FIG. 3 is a flowchart 300 of an example of a patient monitoring and care method. The flowchart 300 starts at module 302 with arrival of a patient. The arrival of a patient typically involves identification of the patient and association of the patient with new or existing health records. The patient is typically prepped by a nurse and is given other standard materials (e.g., a gown).

The flowchart 300 continues to module 304 with assigning a patient devices docking station to the patient. The patient devices docking station can be affixed to an IV pole that is also assigned to the patient, provided in the room or bed to which the patient is assigned, or otherwise provided in proximity to the patient or a caregiver. A suitable device for assigning a patient devices docking station to the patient is the nurse station 112.

The flowchart 300 continues to module 306 with applying a wearable mount to the patient's body. In a specific implementation, the wearable mount is applied to the patient's upper chest. In an alternative, the wearable mount is applied to some other part of the patient's body or to an item or garment of the patient. It may be noted that a garment or other item is more likely to cause erroneous patient position readings than if the wearable is affixed directly to the patient. However, some devices, such as a cast, are relatively rigid, so they can provide relatively reliable data associated with the position of a body part. Wearable mounts are described later in more detail. A suitable person for applying the wearable mount to the patient's body is a first nurse.

The flowchart 300 continues to module 308 with initializing a first wearable device. Initializing the first wearable device can entail pairing it with an endpoint device. The first wearable device can be accessed by opening a patient devices docking station door. (A door is desirable to prevent wearable devices from falling out and may include a lock to prevent tampering or theft.) Initialization generally entails interfacing with the endpoint device, which acts as a computer while docked (and could be locked to, or permanently installed in, the patient devices docking station to prevent tampering or theft). The first nurse then undocks (picks up) the first wearable device and closes (and locks, if applicable) the patient devices docking station door. A suitable person for initializing the first wearable device is the first nurse.

The flowchart 300 continues to module 310 with attaching the first wearable device to the wearable mount on the patient's body. In a specific implementation, the first wearable device snaps securely ("locks") into place. A suitable person for attaching the first wearable device to the wearable mount on the patient's body is the first nurse.

The flowchart 300 continues to module 312 with removing the first wearable device from the wearable mount after a time. The time can be until, for example, a next shift, during which time a second nurse checks in on the patient. In a specific implementation, the first wearable device is unlocked with a physical key, though it could be accomplished with physical pressure, a magnetic device, wirelessly transmitting instructions to an electronic lock to disengage, or some other applicable technology. A suitable person for unlocking the first wearable device is the second nurse (though it could be the first nurse at a later time, as well).

The flowchart 300 continues to module 314 with sanitizing the first wearable device. Sanitizing the first wearable device can be accomplished by disinfecting the first wearable device with a wipe. Instead or in addition, the patient devices docking station could include a UV bulb that sanitizes wearable devices using UV radiation while the devices are docked and the patient devices docking station door is closed. A suitable person for sanitizing the first wearable device is the second nurse (though it could be the first nurse at a later time, as well) and, alternatively or in addition, a suitable device for sanitizing the first wearable device is patient devices docking station.

The flowchart 300 continues to module 316 with initializing a second wearable device. Initializing the second wearable device can entail pairing it with the endpoint device. The second wearable device can be accessed by opening a patient devices docking station door. Initialization generally entails interfacing with the endpoint device, which acts as a computer while docked. The second nurse then docks the first wearable device and undocks the second wearable device and closes the patient devices docking station door. A suitable person for initializing the second wearable device is the second nurse.

The flowchart 300 continues to module 318 with attaching the second wearable device to the wearable mount on the patient's body. A suitable person for attaching the second wearable device to the wearable mount on the patient's body is the second nurse.

The flowchart 300 continues to module 320 with removing the second wearable device from the wearable mount after a time and sanitizing the second wearable device. The flowchart 300 then returns to module 308 and continues as described previously. Obviously, when the patient is discharged or otherwise does not need continued monitoring, the flowchart 300 ends (not shown).

Figure 4:
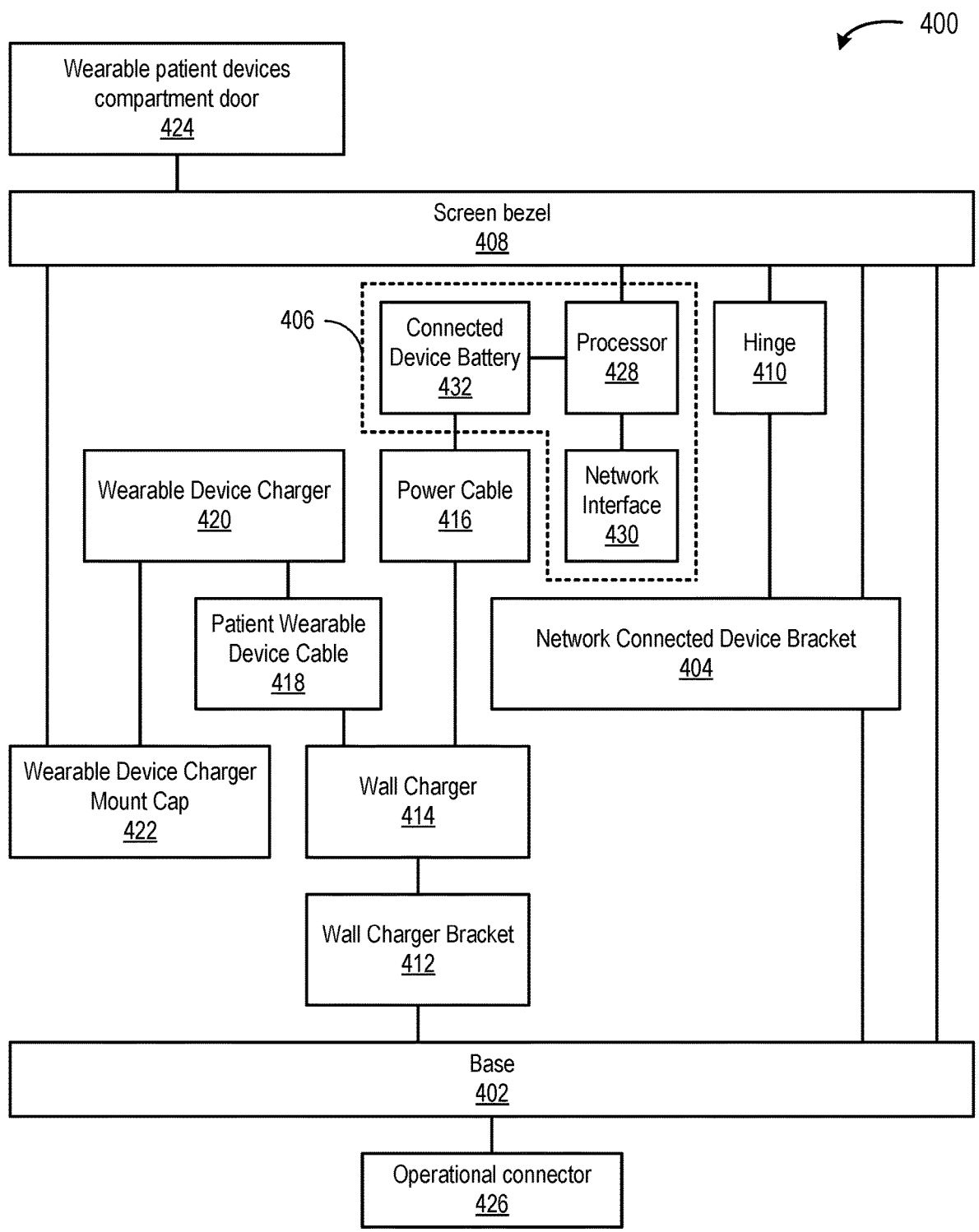
FIG. 4 is a diagram of an example of a dedicated patient device docking station.

FIG. 4 is a diagram 400 of an example of a patient device docking station. The diagram 400 includes a base 402; a network connected device bracket 404 connected to the base 402; a network connected device 406; a screen bezel 408 connected to the base 402, the network connected device bracket 404, and the network connected device 406; and a hinge 410 connecting the network connected device bracket 404 to the screen bezel 408. The diagram 400 further includes a wall charger bracket 412 connected to the base 402, a wall charger 414 connected to the wall charger bracket 412, a charging cable 416 connected to the network connected device 406 and the wall charger 414, a wearable device cable connected to the wall charger 414, a wearable device charger connected to the wearable device cable 418, a wearable device charger mount cap 422 connected to the screen bezel 408 and the wearable device charger 420, a wearable patient devices compartment door 424 connected to the screen bezel 408, and an operational connector 426 connected to the base 402.

The base 402 is intended to represent a discrete or monolithic (with one or more other depicted components) structure that acts as a platform for attachment of other patient device docking station components. In a specific implementation, the base 402 is specifically designed to house a particular smartphone form factor and/or wall charger. In alternatives, the base 402 can be for an applicable network connected device other than a smartphone and some other applicable device for powering the network connected device and docked wearable devices.

The network connected device bracket 404 is intended to represent hardware for receiving the network connected device 406. In a specific implementation, the network connected device bracket 404 is implemented as an IPHONE® Rev 15.0 Phone Mount Bracket. Of course, the network connected device bracket 404 in this specific implementation includes a specific smartphone; any applicable smartphone bracket could be used instead for other smartphone implementations. Alternatives include an applicable bracket suitable for housing the network connected device 406, which need not be a smartphone.

The network connected device 406 is intended to represent a paired endpoint device. See paired patient devices 106, described above with reference to FIG. 1. In a specific implementation, the network connected device 406 is implemented as an iPhone8 Plus. Alternatives include an applicable smartphone suitable for carrying out the function of a paired patient device; some implementations include more than one smartphone per docking station. Other alternatives include one or more applicable network connected devices that are not smartphones.

The screen bezel 408 is intended to represent a top cover for other patient device docking station components. The component is described as a "screen bezel" because in a specific implementation the screen of the network connected device 406 (e.g., a smartphone screen) is visible through an opening in the screen bezel 408. The screen bezel may also be fabricated with holes to facilitate direct contact between patient wearable devices (not shown) and the wearable device chargers 420 when the patient wearable devices are docked. In a specific implementation, the screen bezel 408 is specifically designed to house a particular smartphone form factor and patient wearable device form factors. Alternatives include designs for one or more applicable network connected devices. In an alternative, rather than providing an opening through which a screen of the network connected device 406 can be seen, the screen bezel 408 includes the screen, which is coupled to the network connected device 406 (and the network connected device may or may not have its own dedicated screen). In such an alternative, the screen bezel could be referred to as a "screen display structure."

The hinge 410 is an optional component that facilitates assembly of the screen bezel 408 onto the base 402 or removal thereof. In a specific implementation, the hinge 410 is at least in part fabricated and may or may not include a compression spring. Alternatives include an applicable spring, tab, or latch that facilitates assembly of the screen bezel 408 onto the base 402 or removal thereof.

The wall charger bracket 412 is intended to represent hardware for receiving the wall charger 414. In a specific implementation, the wall charger bracket 412 is specifically designed to retain an ANKER® Atom PD4. Alternatives would be designs suitable for retaining some other wall charger form factor.

The wall charger 414 is intended to represent hardware suitable for plugin to an outlet and to the network connected device 406 via the power cable 416 and to patient wearable devices (not shown) via the wearable device cables 418. In a specific implementation, the wall charger 414 is implemented as an ANKER® Atom PD4. Alternatives include an applicable wall charger suitable for powering the network connected device 406 (and charging patient wearable devices, not shown, using the wearable device chargers 420) via an electrical outlet or other power source.

The power cable 416 is intended to represent a cable or other conductor that connects the wall charger 414 with the network connected device 406. In a specific implementation, the power cable 416 is implemented as a 90 degree Lightning to USB C cable. Alternatives include an applicable cable or other conductor suitable for providing power from a power source to the network connected device 406. It is also possible to utilize wireless charging, which would entail replacing the power cable 416 with appropriate technology to enable wireless recharging.

The patient wearable device cable 418 is intended to represent a cable or other conductor that connects the wall charger 414 with the wearable device chargers 420. In a specific implementation, the patient wearable device cable 418 is implemented as a 0.3 meter cable with USB-A. It may be noted that, in this specific implementation, the wearable device charger 420 and the patient wearable device cable 418 are provided as a composite device, an Apple Watch Charger 0.3 meter with USB-A. Alternatives include an applicable cable or other conductor suitable for providing power from a power source to patient wearable devices (not shown) via the wearable device chargers 420.

The wearable device chargers 420 are intended to represent a contact charger for patient wearable devices (not shown). In a specific implementation, the wearable device chargers 420 are implemented as Apple Watch Chargers. Alternatives include an applicable charger suitable for charging patient wearable devices. In a specific implementation, the wearable device chargers 420 include two chargers, but variants with only one or more than two are possible. For example, if a patient has one device attached to them at a time, a single charger can be used for the patient wearable device that is not in use. As another example, if a patient has two patient wearable devices attached to them at the same time, it may be desirable to have a total of four patient wearable devices, with two docked while the other two are deployed.

The wearable device charger mount caps 422 are intended to represent a support structure for the wearable device chargers 420. In a specific implementation, the wearable device charger mount caps 422 are implemented as iPhone Rev 15.0 Watch charger mount caps. Alternatives include applicable support structures for the wearable device chargers 420. The wearable device chargers 420 and wearable device charger mount caps 422 can be implemented as a composite or monolithic device if appropriately configured.

The wearable patient devices compartment door 424 is intended to represent a mechanism for covering docked patient wearable devices. The wearable patient devices compartment door 424 can be useful for preventing patient wearable devices from falling out of the compartment, protecting the patient wearable devices from harm, and for acting as a theft deterrent. In a specific implementation, when the wearable patient devices compartment door 424 is closed, a UV bulb (not shown) can be activated to sanitize wearable patient devices within the compartment.

The operational connector 426 is intended to represent a mechanism for connecting the base to a surface or other device. The operational connector 426 can include rubber feet that provide a bit of friction if the patient device docking station is placed on a surface. Instead or in addition, the operational connector 426 can include a gasket that fits around an IV pole to facilitate a rigid, rotatable, or otherwise adjustable attachment of the patient device docking station to the IV pole.

Referring back to the network connected device 406, the network connected device 406 can include a hardware processor 428, a network interface 430, and a network connected device battery 432. In a specific implementation, these components are necessary for a desired functionality that includes receiving signals from the wearable patient devices via antennas of the network interface 430 and applicable radio components, which are considered part of the network interface 430, processing the signals using the hardware processor 428 and applicable hardware circuitry, firmware, or software, and ensuring the power supply is uninterrupted by utilizing the network connected device battery 432, which is important in implementations in which the network connected device 406 must be mobile (e.g., affixed to an IV pole, attached to a wheeled cart of bed, etc.). The network connected device 406 may or may not also include a screen (see the discussion of the screen above with reference to the screen bezel 416). In a specific implementation, the network connected device 406 includes memory and non-volatile storage. In an alternative, the network connected device 406 does not include non-volatile storage.

Figure 5:
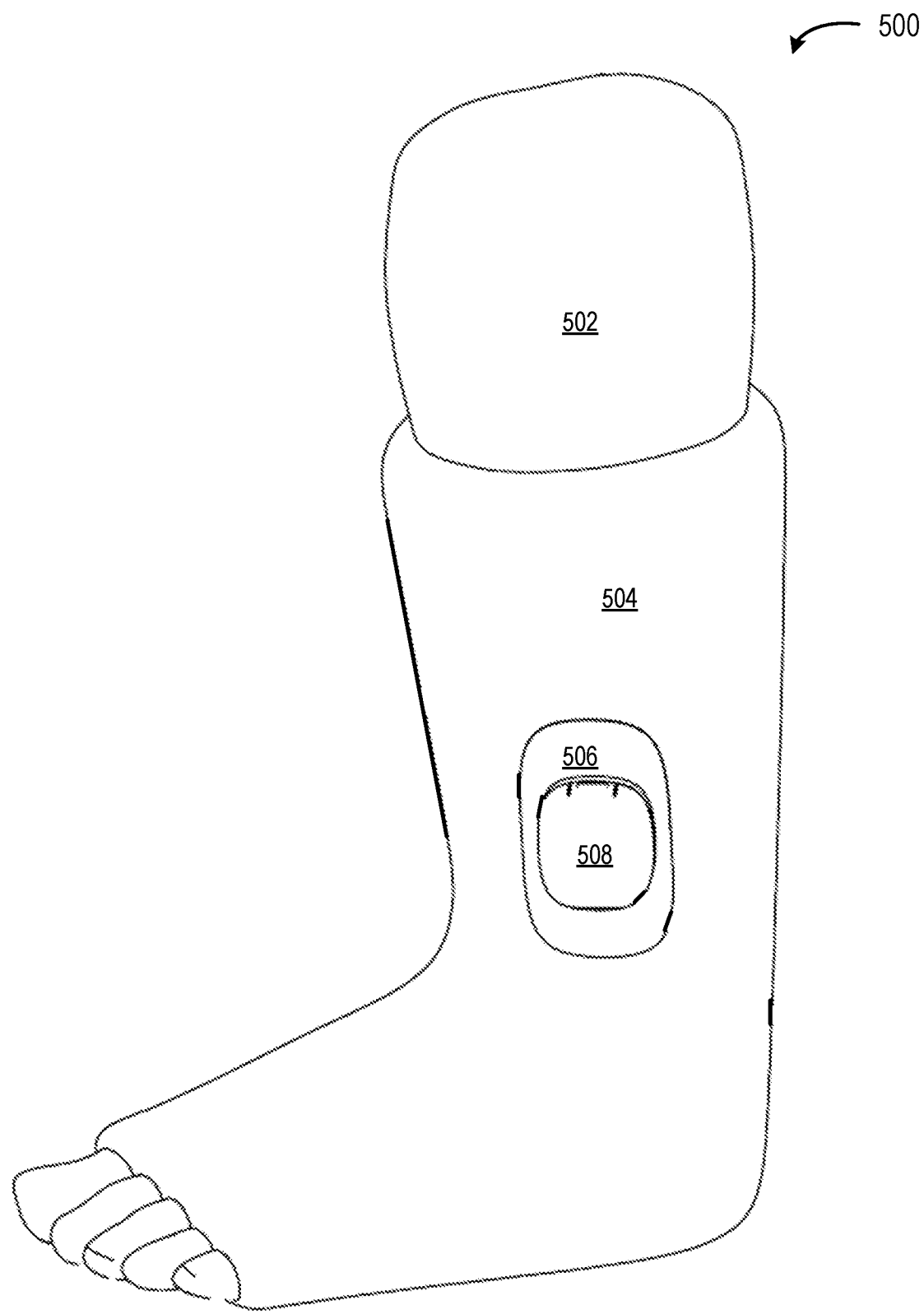
FIG. 5 is a diagram of an example of a wearable device mount other than upper chest.

FIG. 5 is a diagram 500 of an example of a wearable device mount other than upper chest. The diagram 500 includes a patient's leg 502, a cast on the patient's leg 504, a wearable device mount 506, and a patient wearable device 508.

As was described previously, a wearable device mount is typically adhered to the upper chest of a patient. In some instances, such as if you have an uncooperative patient, you may adhere the wearable device mount to a location that is difficult to reach, such as middle back. In yet other instances, the device may be attached to some other location, which is represented by the illustration in FIG. 5. Specifically, the patient's leg 502 has a relatively rigid device attached thereto in the form of the cast on the patient's leg 504. Because the device is relatively rigid, it is a suitable place to affix the wearable device mount 506 and, therefore, the patient wearable device 508. Also, this is likely the portion of the body for which monitoring may be desired, taking some of the emphasis off of pressure ulcer prevention in favor of injured body part monitoring.

In an alternative, the wearable device mount 506 is fabricated into a device, such as a prosthetic. It would become unnecessary to attach the wearable device mount in such an alternative, but the wearable devices can be affixed to the mount in much the same manner as with a mount that is affixed using an adhesive, strap, or other temporary attachment technology.

Figure 6:
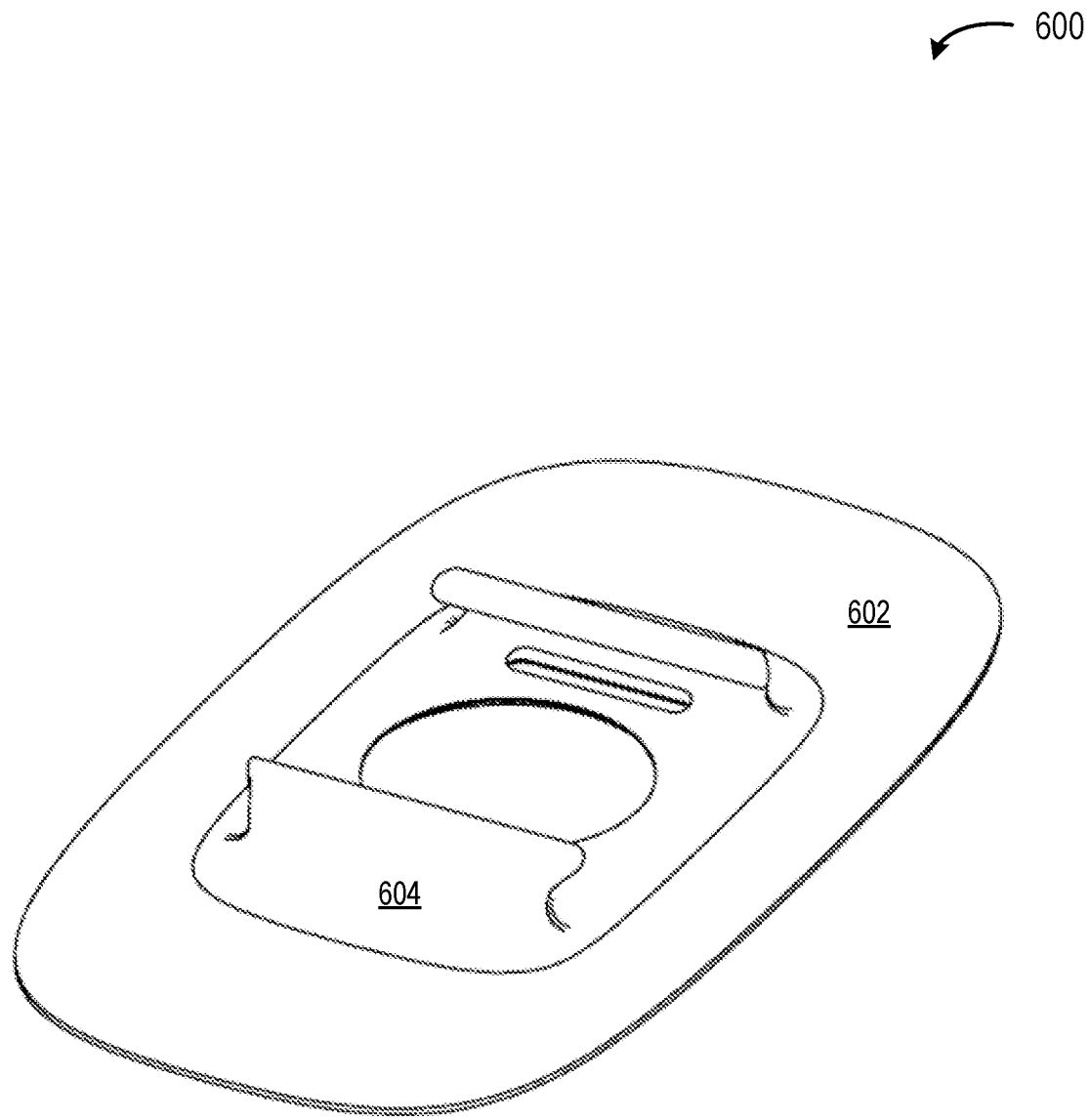
FIGS. 6-8 are diagrams of examples of a wearable patient device mount.
Figure 7:
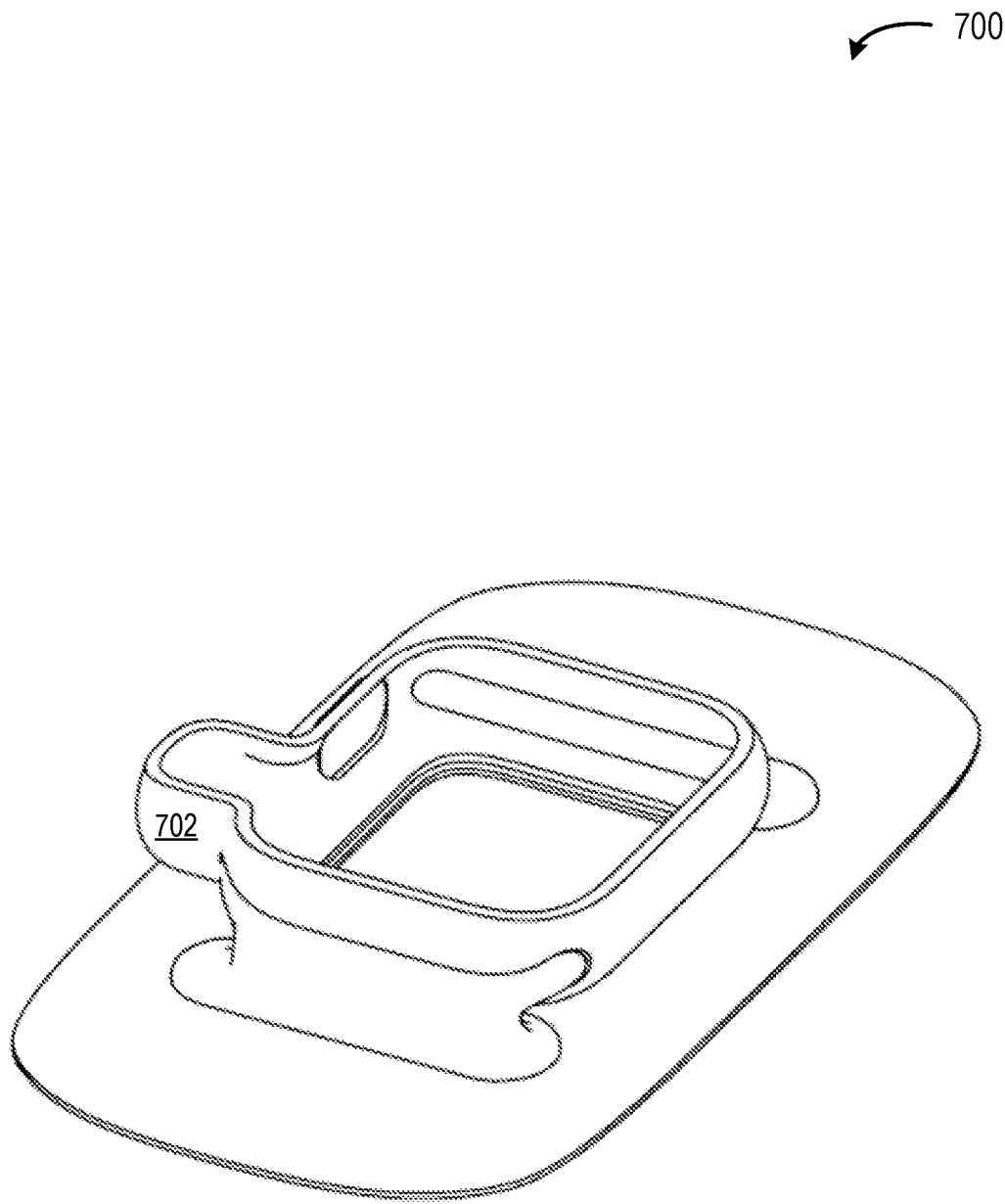
Figure 8:
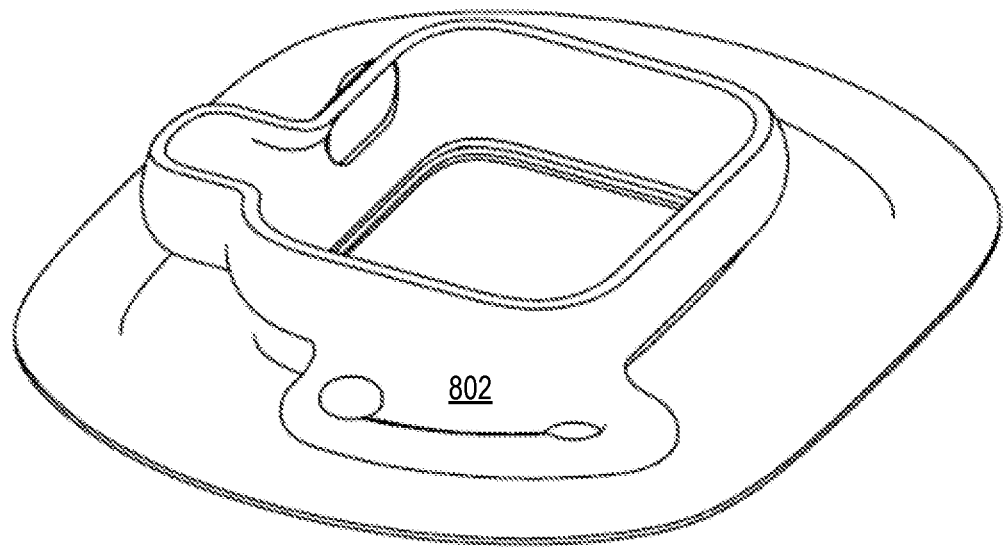

FIGS. 6-8 are diagrams of examples of a wearable patient device mount. The diagram 600 includes an adhesive backing 602 and a wearable device mounting frame 604. In a specific implementation, the adhesive backing 620 includes a sheet that is removed prior to adhering the wearable device mount to a patient. The sheet (not shown) can prevent the adhesive from losing its adhesive properties by covering it and protecting it from dust or other contamination. The wearable device mounting frame 604 is designed for use with an apple watch, which includes a form factor and ridges that enable the apple watch to be snapped into the wearable device mounting frame 604. Alternatives include adjustments to the wearable device mounting frame 604 to receive a form factor other than that of an apple watch.

The diagram 700 is similar to the diagram 600 but includes an oversized knob 702 that facilitates manipulation of a mounted wearable device by a person wearing gloves, which is typical of nursing staff.

The diagram 800 is similar to the diagram 700 but includes a snap-and-twist device 802 that enables a wearable device to be more securely seated in the mount.

Figure 9:
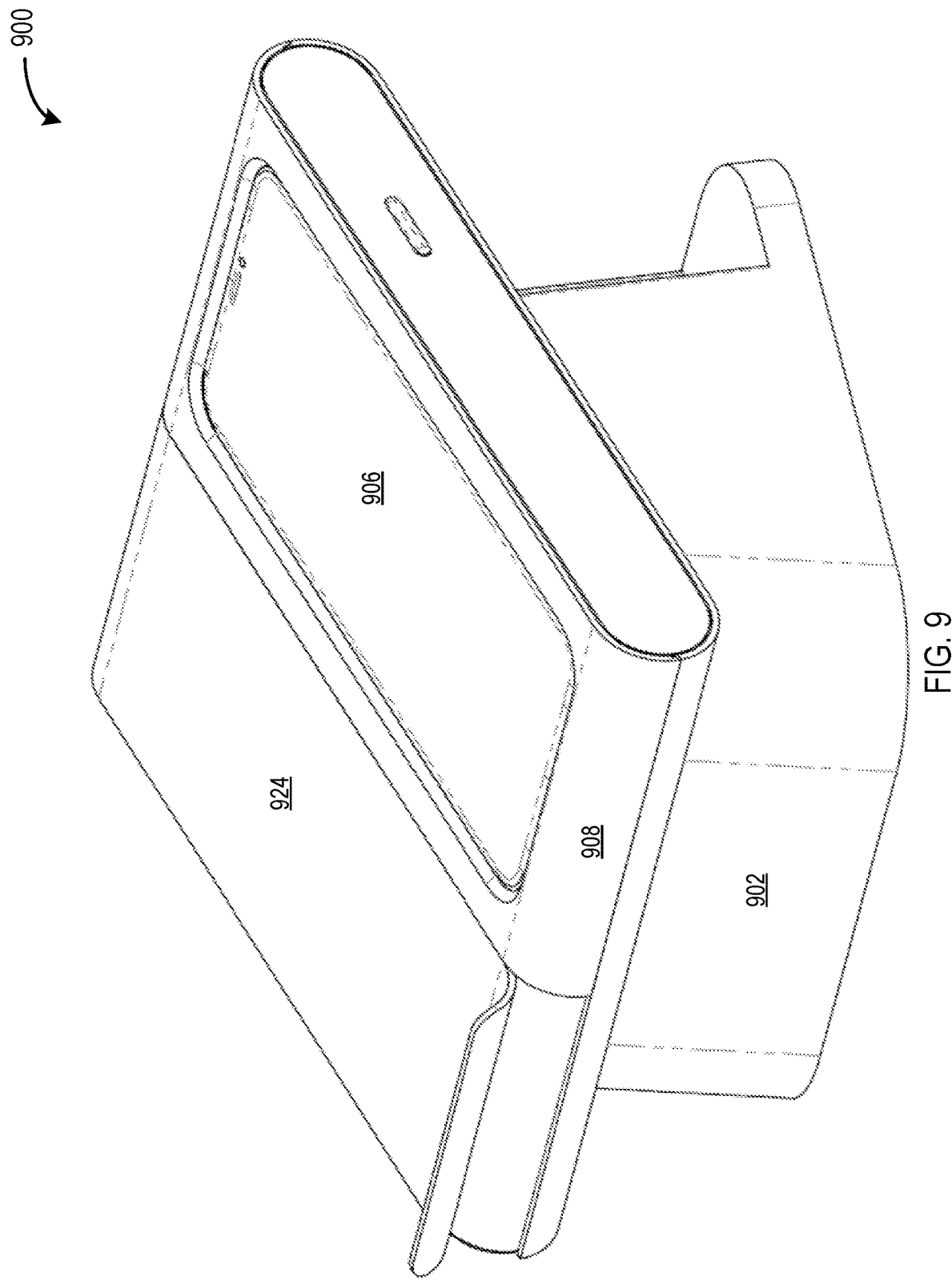
FIGS. 9 and 10 are diagrams of an example of a bedside patient mobility monitor.
Figure 10:
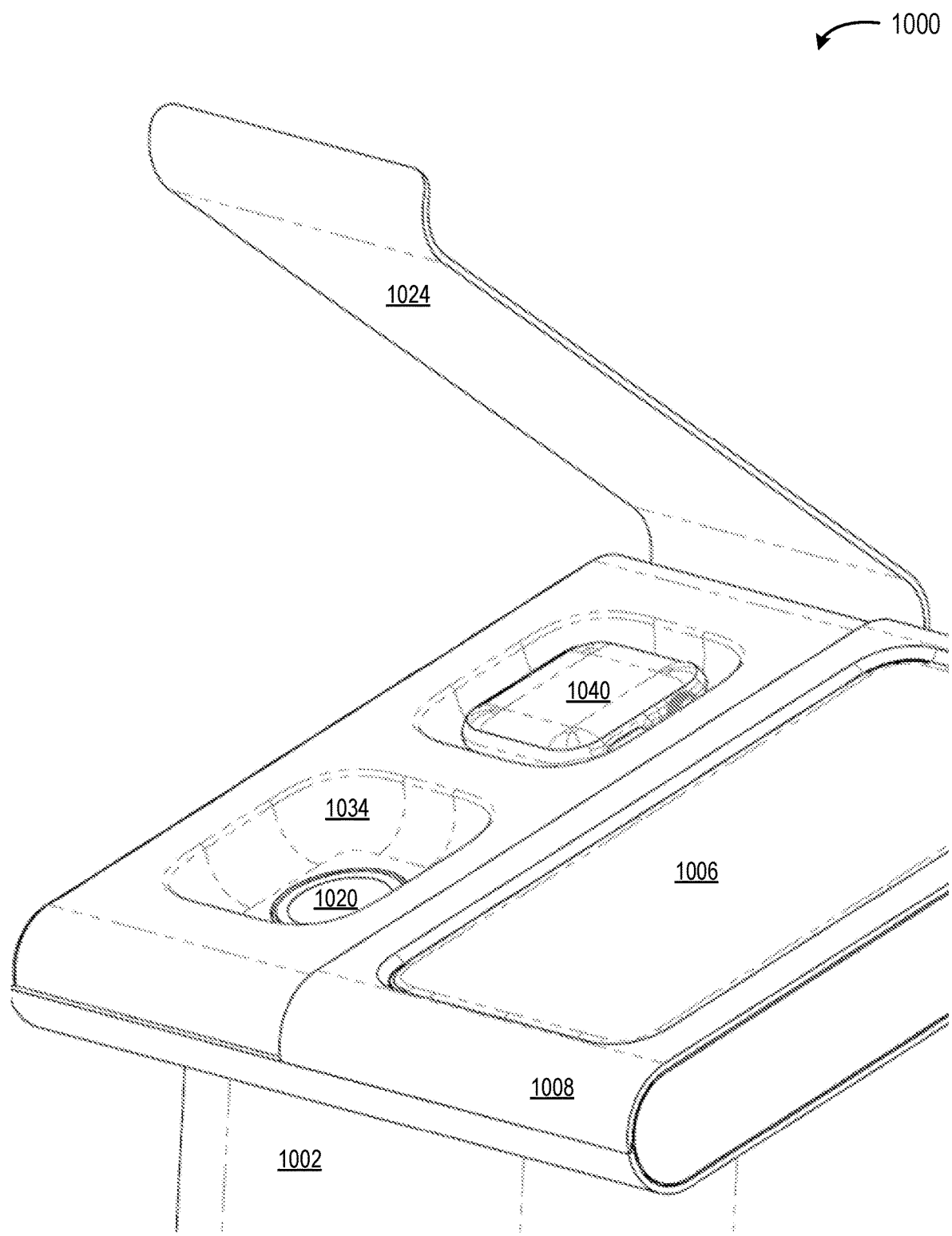

FIGS. 9 and 10 are diagrams 900 and 1000 of examples of a bedside patient mobility monitor. The diagram 900 includes a base 902, a smartphone 906, a screen bezel 908, and a wearable patient devices compartment door 924. In a specific implementation, the smartphone 906 represents a paired patient device and the other components represent a device docking station. See, e.g., FIG. 1, paired patient devices 106 and devices docking station 108. See also, e.g., FIG. 4, wearable base 402, network connected device 406, screen bezel 408, and wearable patient devices compartment door 424. As was mentioned previously, the patient mobility monitor need not explicitly be at "bedside" and could instead be located at a nurse station.

In this example, the base 902 is configured for placement on a surface. In alternatives, the base 902 is instead attached to an IV pole. The base 902 is optional in the sense the components could be held together in some fashion without attaching them to a base. The smartphone 906 is intended to represent one of many possible network connected devices suitable for use as a paired patient device. The screen bezel 908 is intended to represent one of many possible form factors for displaying a screen of a network connected device or a screen to which the network connected device is coupled (so as to enable monitoring by a person who can see the screen). Because, in this example, the screen is that of the smartphone 906, the screen bezel basically provides an opening or transparent cover through which the smartphone screen can be viewed and, in an implementation in which the screen is a touchscreen, used as an input device. The wearable patient devices compartment door 924 is intended to represent a door to a compartment in which wearable patient devices are docked. In a specific implementation the compartment is a concavity formed within the screen bezel. In an alternative, the compartment is a flat surface of the screen bezel and the wearable patient devices compartment door 924 is concave enabling wearable devices to fit within the compartment. In any case, the compartment is defined by a concavity within the screen bezel, if any, and the wearable patient devices compartment door 924 when closed.

The diagram 1000 includes a base 1002, a smartphone 1006, a screen bezel 1008, and a wearable patient devices compartment door 1024. Although substantially similar to the example of FIG. 9, unlike the wearable patient devices compartment door 924 of diagram 900, the wearable patient devices compartment door 1024 is open exposing a concavity 1034 into which a wearable device can be located, a wearable device charger surface 1020, and a wearable device 1030. See, e.g., FIG. 4, wearable device charger 420.

What is claimed is:

1. A system comprising:
a patient wearable sensor device that includes a sensor or trackable component used to facilitate a determination regarding patient physiological data, wherein, in operation, the patient wearable sensor device is affixed to a patient associated with the patient physiological data;
a paired patient device that includes a receiver for at least a subset of the patient physiological data, wherein, in operation, the paired patient device is within short-range radio frequency (RF) communication with the patient wearable sensor device;
a devices docking station that includes a dock configured to couple the patient wearable sensor device to the devices docking station and wherein the devices docking station is configured to recharge the patient wearable sensor device when coupled;
wherein the patient wearable sensor device is a first patient wearable sensor device, comprising a second patient wearable sensor device, wherein, in operation, the first patient wearable sensor device is affixed to the patient in a deployed mode and the second patient wearable sensor device is coupled to the devices docking station in an undeployed mode;
a smart patient care cart comprising a mobile unit that includes an ultraviolet (UV) disinfection unit powered by a battery connected to the smart patient care cart, wherein the patient wearable sensor device can be placed within a chamber of the smart patient care cart that receives UV radiation from the UV disinfection unit that automatically disinfects the patient wearable sensor device when the smart patient care cart is stationary and the patient wearable sensor device is placed within the chamber.

2. The system of claim 1, comprising a nurse station.

3. The system of claim 1, comprising a lift tracker station.

4. The system of claim 1, comprising an agnostic aggregation station.

5. The system of claim 1, comprising a patient datastore, a facility datastore, a caregiver datastore, a device datastore, a patient state datastore, a patient management datastore, a facility management datastore, a caregiver management datastore, an electronic health record (EHR) system datastore, a health/fitness datastore, and an agnostic aggregation datastore.

6. The system of claim 1, wherein the patient wearable sensor device is a short-range device (SRD) that includes a three-axis accelerometer, an orientation sensor, a datastore of detected stimuli, and a radio frequency (RF) transceiver.

7. The system of claim 1, wherein the paired patient device is configured upon startup using a technique that involves scanning a QR code to request a unique certificate that allows the paired patient device to be trusted within a facility.

8. The system of claim 1, wherein the paired patient device is implemented as a network connected device with a screen and a battery.

9. The system of claim 1, wherein the paired patient device includes a bedside tablet computer paired with the patient wearable sensor device.

10. The system of claim 1, comprising a mesh network that includes the paired patient device, wherein the paired patient device communicates with a plurality of devices including the patient wearable sensor device and a nurse station.

11. The system of claim 1, wherein when the devices docking station is recharging the patient wearable sensor device the patient wearable sensor device is in an undeployed mode.

12. The system of claim 1, wherein, in operation, the patient wearable sensor device collects raw patient position data and transmits at least a subset of the raw patient position data to the paired patient device using an RF transceiver and secure communications.

13. The system of claim 1, comprising a patient datastore, wherein the paired patient device provides patient position data to the patient datastore.

14. The system of claim 1, wherein, in operation, the devices docking station is assigned to the patient.

15. The system of claim 1, comprising a wearable mount applied to the patient, wherein the patient wearable sensor device is affixed to the patient via the wearable mount.

16. The system of claim 1, wherein the devices docking station includes a base, a network connected device bracket connected to the base, a network connected device, a screen bezel connected to the base, and a hinge connecting the network connected device bracket to the screen bezel.

17. The system of claim 1, wherein the devices docking station includes a wall charger bracket connected to a base, a wall charger connected to the wall charger bracket, a charging cable connected to the wall charger, a wearable device cable connected to the wall charger, a wearable device charger connected to the wearable device cable, a wearable device charger mount cap connected to the wearable device charger, a wearable patient devices compartment door, and an operational connector connected to the base.

18. The system of claim 1, comprising a wearable patient device mount that includes an adhesive backing and a wearable device mounting frame.

* * * * *